(12) United States Patent
Choi et al.

(10) Patent No.: US 10,139,119 B2
(45) Date of Patent: Nov. 27, 2018

(54) AIR CONDITIONER AND CONTROL METHOD THEREOF

(71) Applicant: LG Electronics, Inc., Seoul (KR)

(72) Inventors: Jieun Choi, Seoul (KR); Sunyoung Moon, Seoul (KR); Ahram Kim, Seoul (KR); Hyungho Park, Seoul (KR); Taeyoon Kim, Seoul (KR); Jinuk Kim, Seoul (KR); Daegeun Son, Seoul (KR); Sanghyuk Son, Seoul (KR); Kyoungho Lee, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 99 days.

(21) Appl. No.: 15/338,112

(22) Filed: Oct. 28, 2016

(65) Prior Publication Data

US 2017/0122592 A1    May 4, 2017

Related U.S. Application Data

(60) Provisional application No. 62/248,463, filed on Oct. 30, 2015.

(30) Foreign Application Priority Data

Nov. 7, 2015   (KR) .................. 10-2015-0156254
Dec. 31, 2015  (KR) .................. 10-2015-0191540

(51) Int. Cl.
*B03C 3/00* (2006.01)
*A61L 9/00* (2006.01)
(Continued)

(52) U.S. Cl.
CPC ....... *F24F 6/04* (2013.01); *A61L 2/10* (2013.01); *F24F 3/166* (2013.01); *F24F 6/00* (2013.01);
(Continued)

(58) Field of Classification Search
CPC .. G05D 23/1931; G05D 23/2401; F17C 9/04; A61L 2/202; A61L 2/208; B01D 53/1487; B01D 53/1412
(Continued)

(56) References Cited

U.S. PATENT DOCUMENTS

2012/0234166 A1    9/2012  Markham et al.
2013/0168234 A1*   7/2013  Lin .................. F24F 3/166
                                            204/228.2
(Continued)

FOREIGN PATENT DOCUMENTS

DE    102014204916 A1   9/2015
JP    2003-14261 A      1/2003
(Continued)

*Primary Examiner* — Monzer R Chorbaji
(74) *Attorney, Agent, or Firm* — Dentons US LLP

(57) ABSTRACT

Provided is an air conditioner. The air conditioner includes a humidification medium, a watering housing to spray water to supply moisture to the humidification medium, a watering motor to rotate the watering housing, a blower fan to blow air, a blower motor to rotate the blower fan, an operation module receiving an instruction from a user, a sterilization module to sterilize the humidification medium, and a control unit to control the watering motor, the blower motor, and the sterilization module according to an instruction inputted to the operation module. Herein, the control unit stops an operation of the watering motor according to the instruction inputted to the operation module, operates the blower motor and the sterilization module when the sterilizing dry mode is set, and stops the operation of the sterilization module after a predetermined sterilizing dry time elapses.

15 Claims, 9 Drawing Sheets

(51) Int. Cl.

| | |
|---|---|
| *F24F 7/007* | (2006.01) |
| *F28D 5/00* | (2006.01) |
| *F24F 6/04* | (2006.01) |
| *F24F 11/30* | (2018.01) |
| *F24F 3/16* | (2006.01) |
| *F24F 6/00* | (2006.01) |
| *F24F 11/77* | (2018.01) |
| *A61L 2/10* | (2006.01) |
| *F24F 13/20* | (2006.01) |
| *F24F 11/52* | (2018.01) |
| *F24F 11/61* | (2018.01) |

(52) U.S. Cl.
CPC ............. *F24F 11/30* (2018.01); *F24F 11/77* (2018.01); *F24F 13/20* (2013.01); *A61L 2202/14* (2013.01); *F24F 11/52* (2018.01); *F24F 11/61* (2018.01); *F24F 2003/1664* (2013.01); *F24F 2003/1667* (2013.01); *F24F 2003/1682* (2013.01); *F24F 2006/006* (2013.01); *F24F 2006/008* (2013.01); *F24F 2006/046* (2013.01)

(58) Field of Classification Search
USPC ............ 96/15, 52, 108, 226; 422/1, 3–4, 28, 422/105, 119, 186.04, 305–306; 454/228; 62/132, 171, 304, 440
See application file for complete search history.

(56) References Cited

U.S. PATENT DOCUMENTS

2013/0206009 A1    8/2013   Huang et al.
2015/0266031 A1    9/2015   Mills et al.

FOREIGN PATENT DOCUMENTS

| JP | 2011-50533 A | 3/2011 |
| JP | 2012-37169 A | 2/2012 |
| KR | 10-2013-0076177 A | 7/2013 |

\* cited by examiner

10,139,119 B2

AIR CONDITIONER AND CONTROL METHOD THEREOF

CROSS-REFERENCE TO RELATED APPLICATIONS

This application claims the benefit of U.S. Provisional Patent Application No. 62/248,463 filed Oct. 30, 2015 and Korean Patent Application Nos. 10-2015-0156254 filed Nov. 7, 2015 and 10-2015-0191540 filed Dec. 31, 2015, which is incorporated herein by reference for all purposes as if fully set forth herein.

BACKGROUND OF THE INVENTION

The present invention disclosed herein relates to an air conditioner and a control method thereof, and more particularly, to an air conditioner for sterilizing and drying a humidification medium containing moisture for humidification.

An air conditioner is an apparatus that changes the interior space into a pleasant environment by allowing air to flow and thus cooling, heating, purifying or humidifying air. Such an air conditioner includes a humidification medium containing moisture for inside humidification. Such a humidification medium may generate odor or propagate bacteria or viruses due to stagnant moisture while not performing humidification.

SUMMARY OF THE INVENTION

The present invention provides an air conditioner for sterilizing and drying a humidification medium containing moisture and a control method thereof.

The objectives of the present invention are not limited to the above-mentioned objectives, and other objectives that are not mentioned will be clearly understood by persons skilled in the art from the following description.

Embodiments of the present invention provide air conditioners including: a humidification medium containing moisture; a watering housing spraying water to supply moisture to the humidification medium; a watering motor rotating the watering housing; a blower fan blowing air to the humidification medium; a blower motor rotating the blower fan; an operation module receiving an instruction from a user and receiving a sterilizing dry mode for sterilizing and drying the humidification medium; a sterilization module sterilizing the humidification medium; and a control unit controlling the watering motor, the blower motor, and the sterilization module according to an instruction inputted to the operation module, wherein the control unit stops an operation of the watering motor according to the instruction inputted to the operation module, operates the blower motor and the sterilization module when the sterilizing dry mode is set, and stops the operation of the sterilization module after a predetermined sterilizing dry time elapses.

In other embodiments of the present invention, provided is control methods of air conditioners. The methods include: stopping an operation of a watering motor for supplying moisture to a humidification medium for humidification; when a sterilizing dry mode for sterilizing and drying the humidification medium is set, blowing air to the humidification medium and sterilizing the humidification medium; and after a predetermined sterilizing dry time elapses, stopping the sterilization.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

DETAILED DESCRIPTION OF PREFERRED EMBODIMENTS

Figure 1:
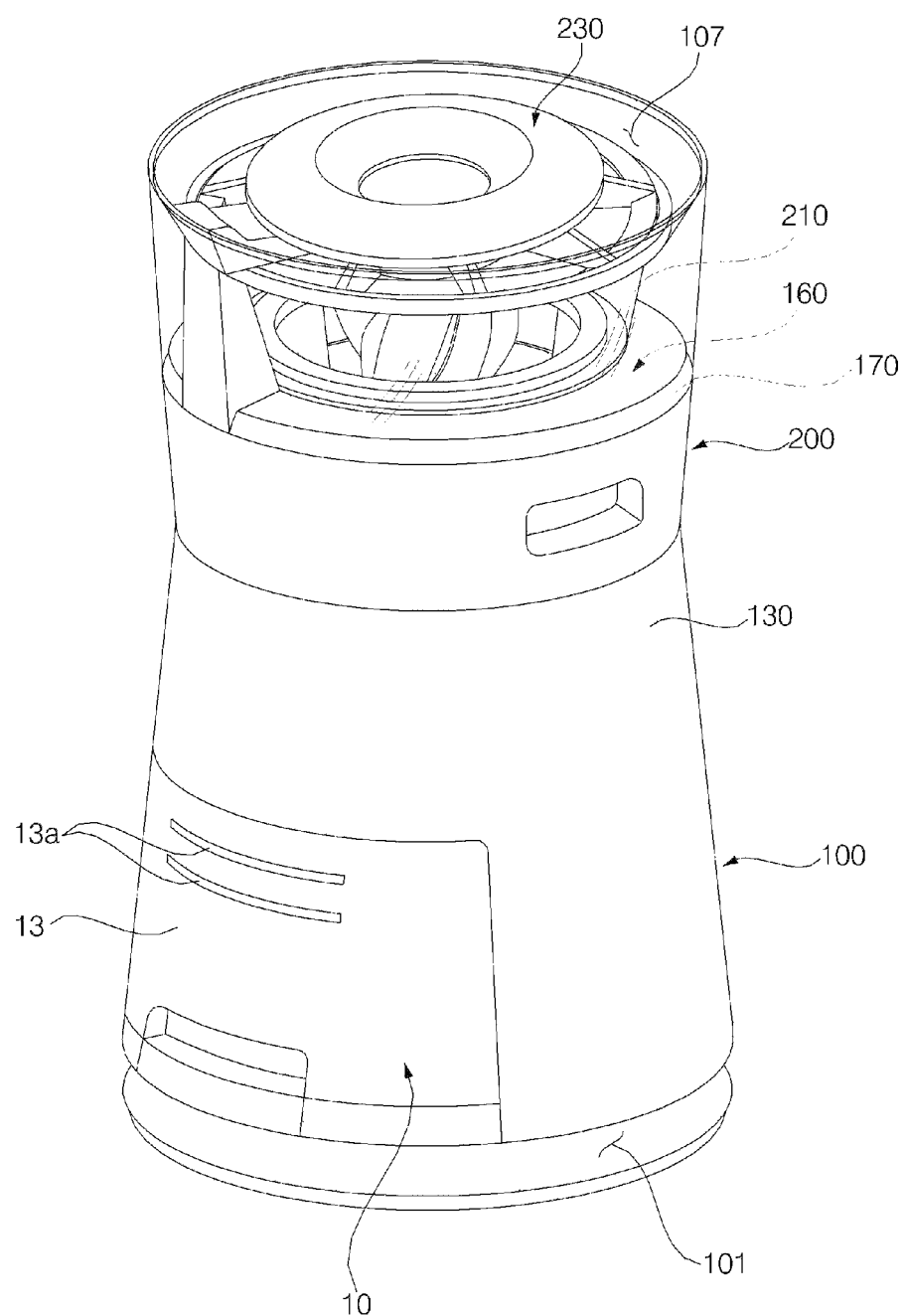
FIG. 1 is a perspective view illustrating an air conditioner according to an embodiment of the present invention.

Advantages and features of the present invention, and implementation methods thereof will be clarified through following embodiments described with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Further, the present invention is only defined by scopes of claims. Like reference numerals refer to like elements throughout.

Hereinafter, air conditioners and control methods thereof according to exemplary embodiments of the present invention will be described in detail with reference to the accompanying drawings.

Figure 2:
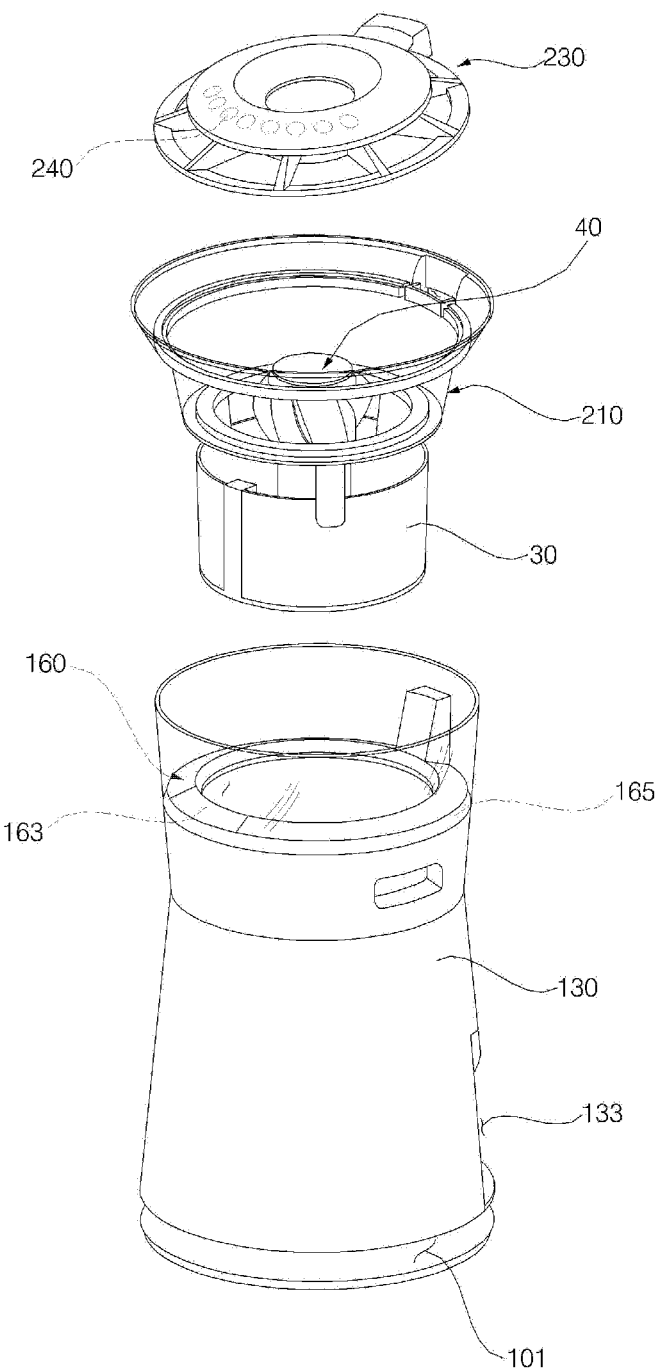
FIG. 2 is a cross-sectional view illustrating the air conditioner shown in FIG. 1.
Figure 3:
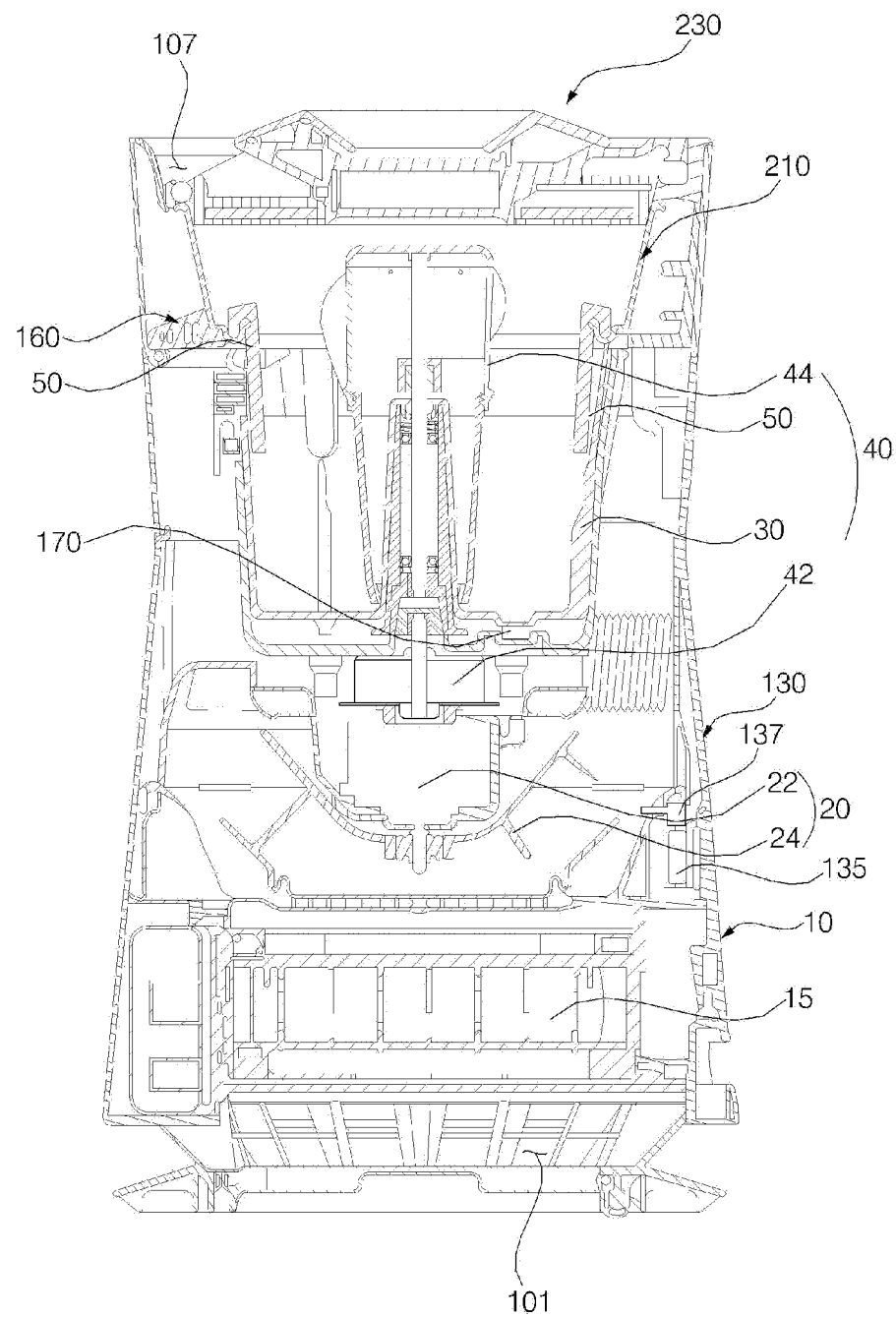
FIG. 3 is a cross-sectional view illustrating the air conditioner shown in FIG. 1.

FIG. 1 is a perspective view illustrating an air conditioner according to an embodiment of the present invention. FIG. 2 is a cross-sectional view illustrating the air conditioner shown in FIG. 1. FIG. 3 is a cross-sectional view illustrating the air conditioner shown in FIG. 1.

An air conditioner according to an embodiment of the present invention may include a cleaning module 100 to receive external air and to clean air, and a humidification module 200 to humidify air cleaned in the cleaning module 100.

The air conditioner may include a base body 130 for supporting the air conditioner from the bottom and forming the appearance, a filter assembly 10 disposed separably from the base body 110 and cleaning air, and a blower unit 20 disposed inside the base body 130 to allow air to flow.

The base body 130 may form the appearance of the air conditioner. The upper part of the base body 130 may be formed of a transparent material through which a use can see the inside. An inlet 101 for receiving external air may be formed at the lower part of the base body 130. A filter installation opening part 133 where the filter assembly 10 is inserted may be formed at one side of the base body 130.

The blower unit 20 may allow air to be entered through the inlet 101 and discharged through an outlet 107. The blower unit 20 may include a blower fan 24 for blowing air and a blower motor 22 for rotating the blower fan 24. Air blown from the blower fan 24 may flow to the humidification module 200. The blower fan 24 may blow air to a humidification medium 50 described later. The blower motor 22 may rotate the blower fan 24 in various rotating speeds.

The filter assembly 10 may clean air entered to the inlet 101. The filter assembly 10 may be disposed at the lower part of the blower unit 20. Air cleaned by the filter assembly 10 may flow to the blower unit 20.

The filter assembly 10 may include a filter cover 13 for shielding the filer installation opening part 133 when installed to the base body 130 and an electrostatic precipitation module 15 for charging foreign materials (for example, dust and so on) in air with electricity to clean the air. The filter assembly 10 may further include a pre-filter (not shown) for filtering foreign materials in air entered through the inlet 101 and a deodorizing filter (not shown) for deodorizing a bad smell in air. A dust detection opening part 13a open to allow external air to flow into a dust detection sensor 135 described later may be formed at the filter cover 13.

The humidification module 200 may include a visual body 210 detachably coupled to the cleaning module 100 and formed of a transparent material through which a user can see the inside, a water tank 30 coupled to the visual body 210 and storing water, a watering unit 40 for drawing water stored in the water tank 30 and spraying the water, a humidification medium 50 wetted with water sprayed from the watering unit 40 to contain a moisture and humidifying passing-through air, and a top cover assembly 230 disposed at the upper end of the visual body 210.

The visual body 210 may be disposed inside the upper part of the base body 130. The lower end of the visual body 210 may be coupled with the water tank 30. The visual body 210 may reflect and scatter water sprayed from the watering unit 40. The humidification medium 50 may be disposed at the lower side of the visual body 210.

The water tank 30 may store water. The water tank 30 may be seated inside base body 130. The upper end of the water tank 30 may be coupled with the visual body 210 so that the water tank 30 may be separated from the cleaning module 100 together with the visual body 210. A space may be formed between the visual body 210 and the water tank 30 and air blown by the blower fan 24 of the blower unit 20 may flow into the space.

The humidification medium 50 may be disposed between the visual body 210 and the water tank 30. The humidification medium 50 may be disposed not to directly contact water stored in the water tank 30. The humidification medium 59 may be wet with water sprayed and scattered by the watering unit 40. The humidification medium 50 may be formed of a material that is capable of containing moisture. Air flowing to the space between the visual body 210 and the water tank 30 may pass through the humidification medium 50. The humidification medium 50 may contain moisture and humidify passing-through air.

The watering unit 40 may include a rotatable watering housing 44 for drawing and spraying water in the water tank 30 and a watering motor 42 for rotating the watering housing 44. The watering housing 44 is rotated by the watering motor 42 to draw and spray water in the water tank 30. The watering housing 44 may spray water to the visual body 210 to supply moisture to the humidification medium 50. The watering motor 42 may be disposed at the lower side of the watering housing 44 and disposed at the upper side of the blower motor 22.

The top cover assembly 230 may cover the upper side of the visual body 210. The top cover assembly 230 may be separably coupled to the visual body 210. An outlet 107 through which air humidified by the watering unit 40 is discharged to the outside may be formed at the top cover assembly 230.

The dust detection sensor 135 may detect a dust concentration in air. The dust detection sensor 135 may be disposed at the outer side surface of the base body 130. The dust detection sensor 135 may be disposed to correspond to the dust detection opening part 13a to detect a dust concentration in external air flowing through the dust detection opening part 13a. The dust detection sensor 135 may detect a dust concentration by each dust particle size and in this embodiment, may distinguish and detect dust concentrations of PM 1.0, PM 2.5, and PM 10.0.

The operation module 240 may receive an instruction from a user. The operation module 240 may be disposed at the upper surface of the top cover assembly 230. Through the operation module 240, a user may input various instructions for controlling operations of the air conditioner.

The display module 160 may display a state of the air conditioner. The display module 160 may be formed in a ring shape and disposed inside the base body 130. The display module 160 may be disposed to allow a user to see it through a transparent portion of the base body 130. A user may check a dust concentration, a current operation mode, or a current setting state through the display module 160.

The display module 160 may include a display unit 163 for displaying a state of the air conditioner through an icon or a letter and a lighting unit 165 for displaying a state of the air conditioner through light of various colors. The display unit 163 may display a dust concentration, an operation state, or a setting state through an icon or a letter. The lighting unit 165 may display a dust concentration or an operation state by emitting light of various colors.

An ion generation module 137 may generate ions to remove bacteria or viruses. The ion generation module 137 may be disposed inside base body 130. The ion generation module 137 may be disposed on a flow passage of air that flows by the blower fan 24 of the blower unit 20. The ion generation module 137 may ionize molecules as high voltage is applied. The ions generated by the ion generation module 137 may flow to the humidification medium 50 by the blower fan 24 of the blower unit 20. Since continuous ion generation is harmful for a user, it may be desirable that the ion generation module 137 operates only in a specific mode such as a sterilizing dry mode described later.

An ultraviolet module 170 may emit ultraviolet light to remove bacteria or viruses. The ultraviolet module 170 may emit ultraviolet light toward water stored in the water tank 30 or the humidification medium 50 to remove bacteria or viruses, which are propagated from the water stored in the water tank 30 or the humidification medium 50. Since continuous emission is harmful for a user, it may be desirable that the ultraviolet module 170 operates only in a specific mode such as a sterilizing dry mode or by a setting.

Hereinafter, the ion generation module 137 and the ultraviolet module 170 may be collectively referred to as a sterilization module. That is, the sterilization module may mean one or both of the ion generation module 137 and the ultraviolet module 170.

Figure 4:
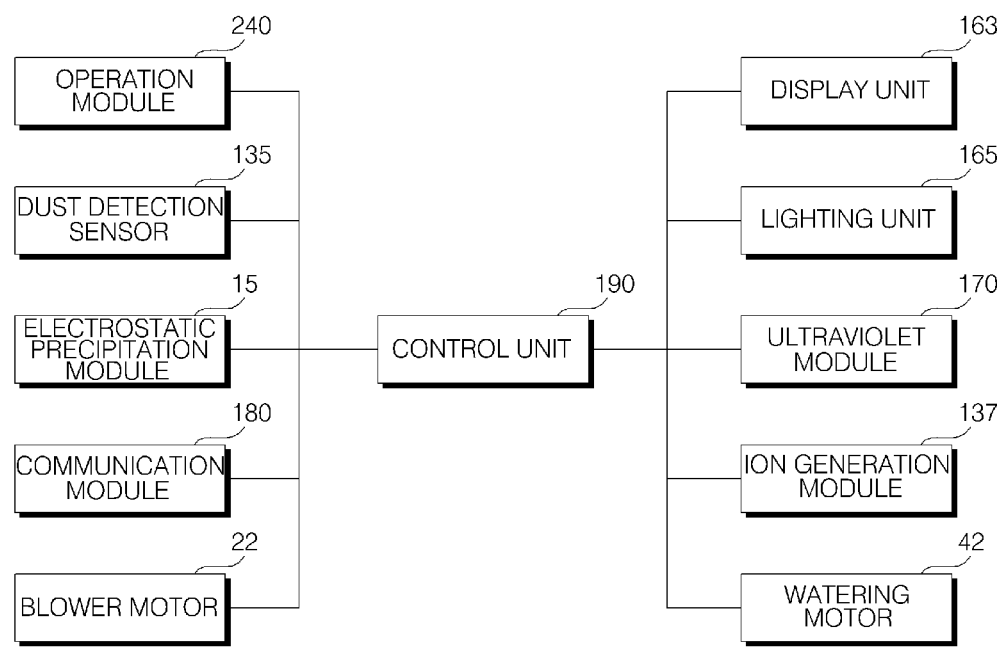
FIG. 4 is a block diagram of an air conditioner according to an embodiment of the present invention.

FIG. 4 is a block diagram of an air conditioner according to an embodiment of the present invention.

Since the operation module 240, the dust detection sensor unit 135, the electrostatic precipitation module 15, the blower motor 22, the watering motor 42, the ion generation module 137, the ultraviolet module 170, the lighting unit 165, and the display unit 163 are identical to the above components, their descriptions will be omitted.

A communication module 180 may be communicably connected to a user's portable device and transmit a state of the air conditioner to the user's portable device. The communication module 180 may receive a user's instruction inputted through a user's portable device. The communication module 180 may be wirelessly connected to a portable device such as a user's mobile phone or tablet through wireless communication such as Wireless LAN (WLAN) (for example, Wi-Fi), 3G, or 4G LTE, Bluetooth, Radio Frequency Identification (RFID), and infrared Data Association (IrDA).

The control unit 190 may control the dust detection sensor 135, the electrostatic precipitation module 15, the blower motor 22, the watering motor 42, the ion generation module 137, and/or the ultraviolet module 170 according to a user's instruction inputted through the operation module 240 or the communication module 180, may notify a user of a state of the air conditioner through the lighting unit 165, the display unit 163, and/or the communication module 180.

Figure 5:
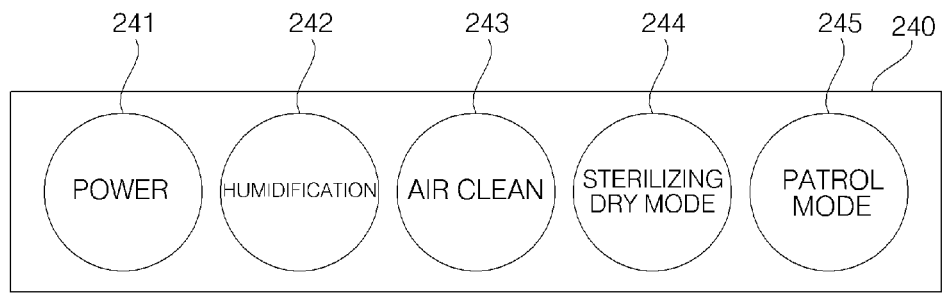
FIG. 5 is a view illustrating an operation module of an air conditioner according to an embodiment of the present invention.

FIG. 5 is a view illustrating an operation module of an air conditioner according to an embodiment of the present invention.

The operation module 240 may include a power button 241 for starting or terminating the entire operation of the air conditioner, a humidification button 242 for starting or terminating a humidification operation for humidifying air, an air clean button 243 for starting or terminating an air clean operation for cleaning air, a sterilizing dry button 244 for setting a sterilizing dry mode for sterilizing and drying a humidification medium, and a patrol button 245 for setting a patrol mode to detect a dust concentration after an operation termination. The operation module 240 may include a button for starting, terminating, or setting various modes or operations in addition to the above-mentioned buttons.

Figure 6:
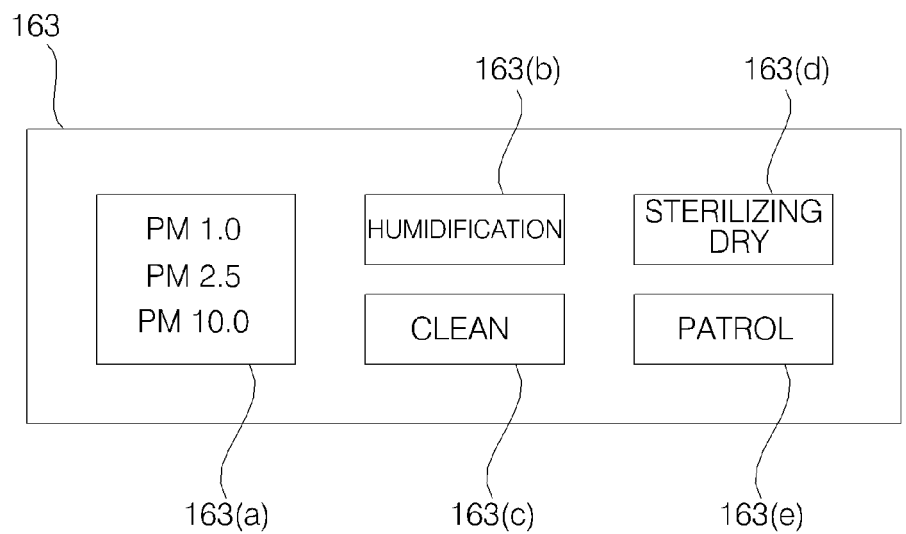
FIG. 6 is a view illustrating a display unit of an air conditioner according to an embodiment of the present invention.

FIG. 6 is a view illustrating a display unit of an air conditioner according to an embodiment of the present invention.

The display unit 163 may include a dust concentration display column 163a for displaying an excessive dust concentration, a humidification display column 163b for displaying that a humidification operation is being performed, an air clean display column 163c for displaying that an air clean operation is being performed, a sterilizing dry display column 163d for displaying that a sterilizing dry mode is set, and a patrol display column 163e for displaying that a patrol mode is set.

The dust concentration display column 163a may display "PM 1.0" or "ultra fine dust" when a dust concentration of PM 1.0 is excessive, display "PM 2.5" or "fine dust" when a dust concentration of PM 2.0 is excessive, and may display "PM 10.0" or "dust" when a dust concentration of PM 10.0 is excessive.

The dust concentration display column 163a, the humidification display column 163b, the air clean display column 163c, the sterilizing dry display column 163d, and the patrol display column 163e may be displayed in letters or icons and in this embodiment, they are displayed in letters. The display unit 163 may include a display column for displaying various modes, an operation or setting state, or an air state in addition to the above-mentioned display columns.

Figure 7:
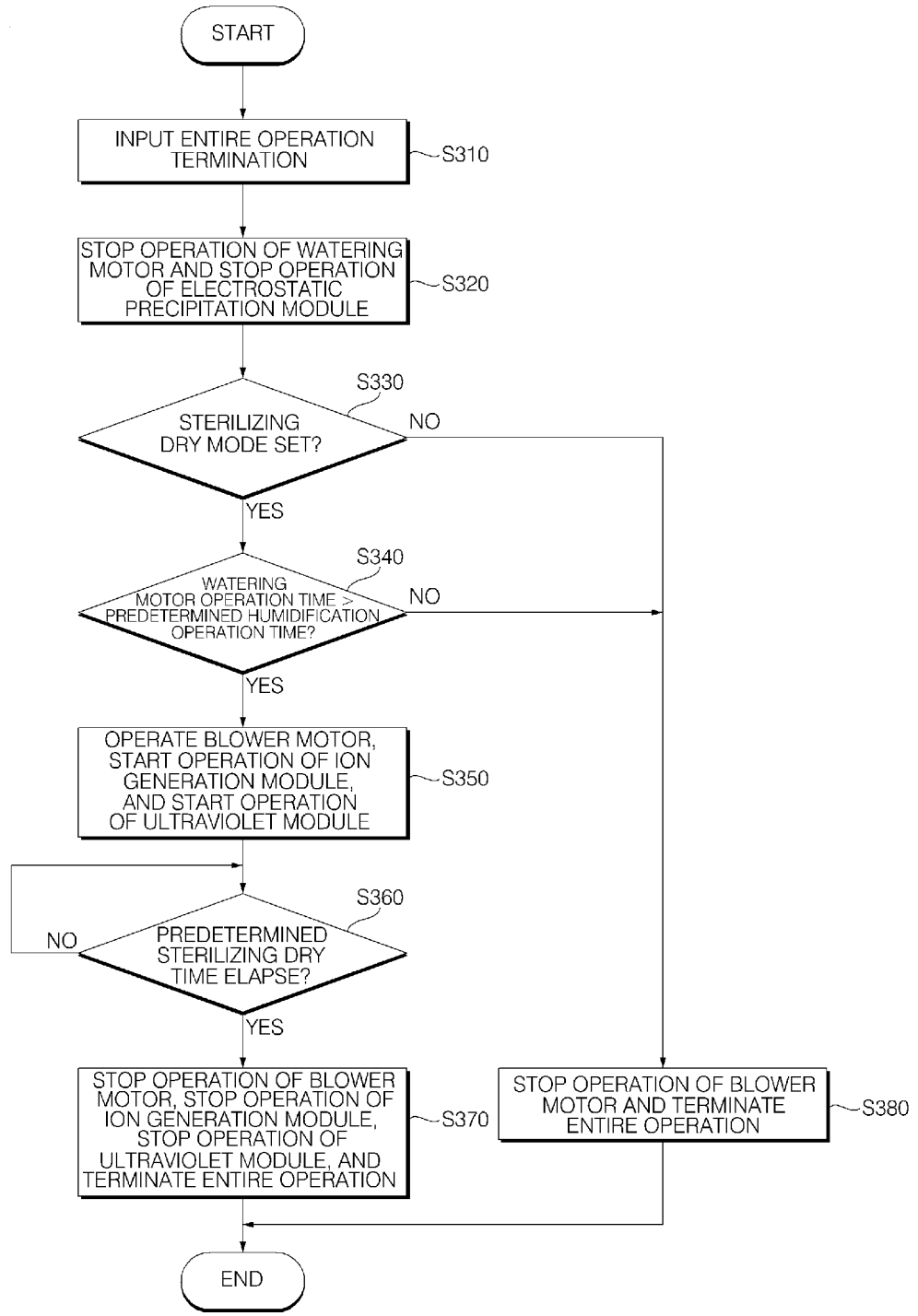
FIG. 7 is a flowchart illustrating a control method of an air conditioner according to an embodiment of the present invention.

FIG. 7 is a flowchart illustrating a control method of an air conditioner according to an embodiment of the present invention.

An instruction for terminating the entire operation may be inputted during an operation of the air conditioner in operation S310. When a user presses the power button 241 of the operation module 240 during an operation of the air conditioner, the operation module 240 may deliver an instruction for terminating the entire operation to the control unit 190.

Before the instruction for terminating the entire operation is inputted, the air conditioner may perform both a humidification operation and an air clean operation, or perform one of them. In this embodiment, description is made based on a case that an instruction for terminating the entire operation is inputted while both a humidification operation and an air clean operation are performed.

Once the entire operation termination instruction is inputted, the control unit 190 may stop an operation of the watering motor 42 and stop an operation of the electrostatic precipitation module 15 in operation S320. The control unit 190 may stop an operation of the watering motor 42 in order to allow the watering housing 44 to stop spraying water. The control unit 190 may stop an operation of the electrostatic precipitation module 15 in order to allow the electrostatic precipitation module 15 to stop charging foreign materials in air with electricity. Once the entire operation termination instruction is inputted, the control unit 190 may allow the display of the humidification display column 163b and the air clean display column 163c of the display unit 163 to disappear.

The control unit 190 may operate the blower motor 22 when the blower motor 22 is in operation.

The control unit 190 may determine whether a sterilizing dry mode is set in operation S330. Before the entire operation termination instruction is inputted after the air conditioner operates, if a user presses the sterilizing dry button 244, the operation module 240 may deliver to the control unit 190 information that a sterilizing dry mode is inputted, and the control unit 190 may set the sterilizing dry mode and display on the sterilizing dry display column 163d of the display unit 163 information that the sterilizing dry mode is set. Once the entire operation termination instruction is inputted, the control unit 190 may determine whether the sterilizing dry mode is set.

According to an embodiment, when a user presses the sterilizing dry button 244 after the entire operation termination, the control unit 190 may determine whether the sterilizing dry mode is set in order to perform the following steps.

When the sterilizing dry mode is set, the control unit 190 may determine whether an operation time of the watering motor 42 is longer than a predetermined humidification operation time before a user presses the power button 241 after an operation of the air conditioner in operation S340. In order to determine whether the humidification medium 50 is wet a lot before the power button 241 is pressed, the control unit 190 may determine whether the watering motor 42 operates more than a predetermined humidification operation time.

When the watering motor 42 operates more than the predetermined humidification operation time, the control unit 190 may start the blower motor 22 and a sterilization module in operation S350. The control unit 190 may operate the sterilization module to sterilize the humidification medium 50. As mentioned above, the sterilization module is the ion generation module 137 and/or the ultraviolet module 170, and in this embodiment, the control unit 190 may operate the ion generation module 137 and the ultraviolet module 170.

When the blower motor 22 stops its operation, the control unit 190 may start an operation of the blower motor 22 and when the blower motor 22 operates, the control unit 190 may operate the blower motor 22 continuously. The control unit 190 may operate the blower motor 22 to allow the blower fan 24 to blow air to the humidification medium 50. The control unit 190 may operate the blower motor 22 to allow the blower fan 24 to rotate at a slow rotation speed. As the blower fan 24 rotates slowly, this may prevent ions generated by the ion generation module 137 from being delivered to a user. When the blower motor 22 rotates the blower fan 24, the blower fan 24 may blow air to the humidification medium 50 to dry it.

The control unit 190 may start an operation of the ion generation module 137 to allow it to generate ions. The ions generated by the ion generation module 137 may flow to the humidification medium 50 by the blower fan 24 of the blower unit 20 to sterilize the humidification medium 50.

The control unit 190 may start an operation of the ultraviolet module 170 to allow it to emit ultraviolet rays to the humidification medium 50. The ultraviolet module 170 may emit ultraviolet rays to the humidification medium 50 to sterilize it.

While the sterilization module operates, the control unit 190 may emit light of a specific color through the lighting unit 165. In this embodiment, the control unit 190 may allow the lighting unit 165 to emit blue color light in order to allow a user to easily notice that a sterilizing dry mode is in operation.

The control unit 190 may determine whether a predetermined sterilizing dry time elapses after the sterilization module operates in operation S360. Since the sterilizing dry mode uses a lot of energy and thus it is desirable that the sterilizing dry mode operates by a predetermined sterilizing dry time, the control unit 190 may determine whether the blower motor 22, the ion generation module 137, and the ultraviolet module 170 operate by the predetermined sterilizing dry time.

When the predetermined sterilizing dry time does not elapse after the sterilization module operates, the control unit 190 may operate the blower motor 22 and the sterilization module.

When the predetermined sterilizing dry time elapses after the sterilization module operates, the control unit 190 may terminate the entire operation completely in operation S370. The control unit 190 may stop an operation of the blower motor 22 to stop the rotation of the blower fan 24, stop an operation of the ion generation module 137, and stop an operation of the ultraviolet module 170. Additionally, the control unit 190 may stop the display of the display unit 163 and the light emission of the lighting unit 165 and allow the air conditioner to enter a standby state.

When the sterilizing mode is not set or the watering motor 42 does not operate longer than a predetermined humidification operation time, the control unit 190 may stop an operation of the sterilization module and terminate the entire operation completely in operation S380. The control unit 190 may stop an operation of the blower motor 22 to stop the rotation of the blower fan 24, stop the display of the display unit 163 and the light emission of the lighting unit 165, and allow the air conditioner to enter a standby state.

Figure 8:
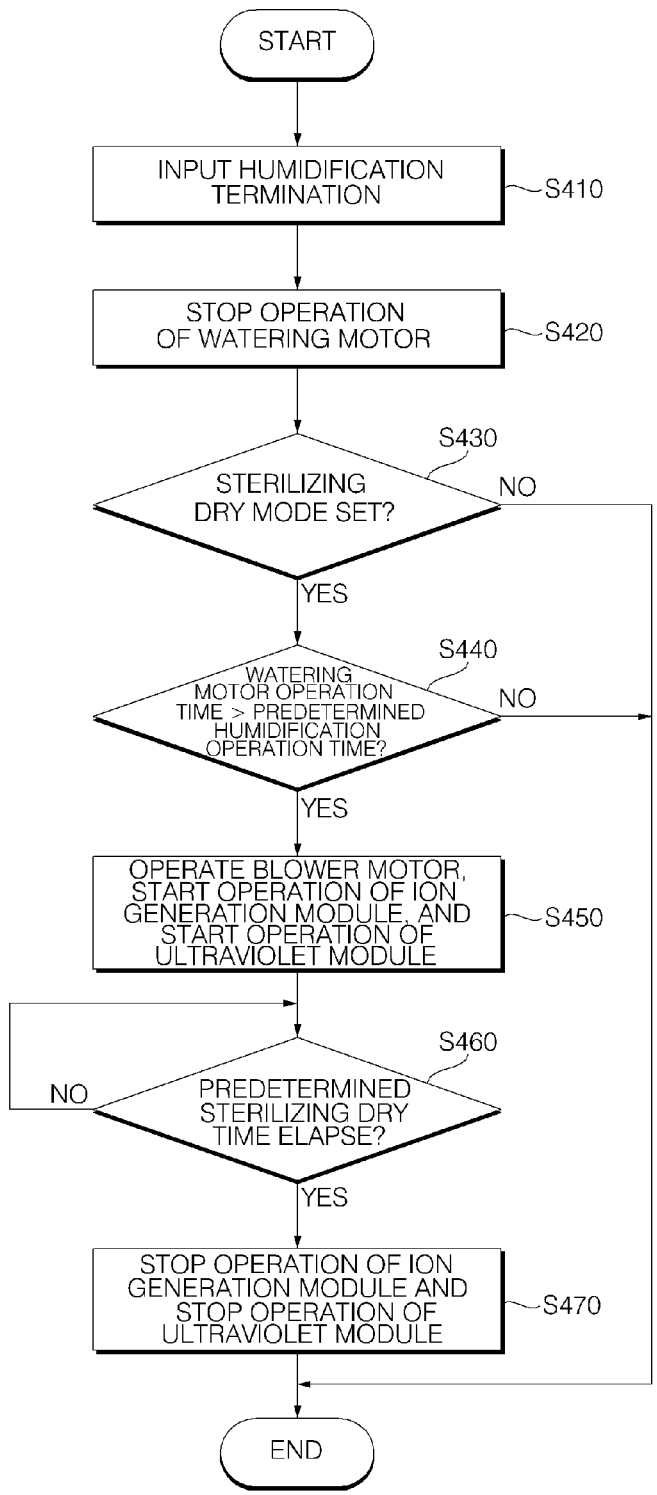
FIG. 8 is a flowchart illustrating a control method of an air conditioner according to another embodiment of the present invention.

FIG. 8 is a flowchart illustrating a control method of an air conditioner according to another embodiment of the present invention.

An instruction for terminating a humidification operation may be inputted during an operation of the air conditioner in operation S410. When a user presses the humidification button 242 of the operation module 240 during the humidification operation or entire operation (for example, both the humidification operation and the air clean operation) of the air conditioner, the operation module 240 may deliver to the control unit 190 information that the instruction for terminating the humidification operation is inputted.

Before the instruction for terminating the humidification operation is inputted, the air conditioner may perform both a humidification operation and an air clean operation, or perform one of them. In this embodiment, description is made based a case that an instruction for terminating a humidification operation is inputted while both a humidification operation and an air clean operation are performed.

Once the humidification operation termination instruction is inputted, the control unit 190 may stop an operation of the watering motor 42 in operation S420. The control unit 190 may stop an operation of the watering motor 42 in order to allow the watering housing 44 to stop spraying water. Once the humidification operation termination instruction is inputted, the control unit 190 may allow the display of the humidification display column 163b of the display unit 163 to disappear.

The control unit 190 may operate the blower motor 22 when the blower motor 22 is in operation.

The control unit 190 may determine whether a sterilizing dry mode is set in operation S430. Before the humidification operation termination instruction is inputted after the air conditioner operates, if a user presses the sterilizing dry button 244, the operation module 240 may deliver to the control unit 190 information that a sterilizing dry mode is inputted, and the control unit 190 may set the sterilizing dry mode and display on the sterilizing dry display column 163d of the display unit 163 information that the sterilizing dry mode is set. Once the humidification operation termination instruction is inputted, the control unit 190 may determine whether the sterilizing dry mode is set.

According to an embodiment, when a user presses the sterilizing dry button 244 after the humidification operation termination, the control unit 190 may determine whether the sterilizing dry mode is set in order to perform the following steps.

When the sterilizing dry mode is not set, continuously, the control unit 190 may operate the blower motor 22 and the electrostatic precipitation module 15 to perform an air clean operation.

When the sterilizing dry mode is set, the control unit 190 may determine whether an operation time of the watering motor 42 is longer than a predetermined humidification operation time before a user presses the power button 241 after an operation of the air conditioner in operation S440. In order to determine whether the humidification medium 50 is wet a lot before the power button 241 is pressed, the control unit 190 may determine whether the watering motor 42 operates more than a predetermined humidification operation time.

When it does not operate more than a predetermined humidification operation time, continuously, the control unit 190 may operate the blower motor 22 and the electrostatic precipitation module 15 to perform an air clean operation.

When the watering motor 42 operates more than the predetermined humidification operation time, the control unit 190 may start the blower motor 22 and a sterilization module in operation S450. The control unit 190 may operate the sterilization module to sterilize the humidification medium 50. As mentioned above, the sterilization module is the ion generation module 137 and/or the ultraviolet module 170, and in this embodiment, the control unit 190 may operate the ion generation module 137 and the ultraviolet module 170.

When the blower motor 22 stops its operation, the control unit 190 may start an operation of the blower motor 22 and when the blower motor 22 operates, the control unit 190 may operate the blower motor 22 continuously. The control unit 190 may operate the blower motor 22 to allow the blower fan 24 to blow air to the humidification medium 50. The control unit 190 may operate the blower motor 22 to allow the blower fan 24 to rotate at an existing rotation speed. The blow fan 24 may rotate as before to allow an air clean operation to continue. When the blower motor 22 rotates the blower fan 24, the blower fan 24 may blow air to the humidification medium 50 to dry it.

The control unit 190 may start an operation of the ion generation module 137 to allow it to generate ions. The ions generated by the ion generation module 137 may flow to the humidification medium 50 by the blower fan 24 of the blower unit 20 to sterilize the humidification medium 50.

The control unit 190 may start an operation of the ultraviolet module 170 to allow it to emit ultraviolet rays to the humidification medium 50. The ultraviolet module 170 may emit ultraviolet rays to the humidification medium 50 to sterilize it.

While the sterilization module operates, the control unit 190 may emit light of a specific color through the lighting unit 165. In this embodiment, the control unit 190 may allow the lighting unit 165 to emit blue color light in order to allow a user to easily notice that a sterilizing dry mode is in operation.

The control unit 190 may determine whether a predetermined sterilizing dry time elapses after the sterilization module operates in operation S460. Since the sterilizing dry mode uses a lot of energy and thus it is desirable that the sterilizing dry mode operates by a predetermined sterilizing dry time, the control unit 190 may determine whether the ion generation module 137 and the ultraviolet module 170 operate by the predetermined sterilizing dry time.

When the predetermined sterilizing dry time does not elapse after the sterilization module operates, the control unit 190 may operate the sterilization module.

When the predetermined sterilizing dry time elapses after the sterilization module operates, the control unit 190 may terminate its operation in operation S470. The control unit 190 may stop an operation of the ion generation module 137 and stop an operation of the ultraviolet module 170. Continuously, the control unit 190 may operate the blower motor 22 and the electrostatic precipitation module 15 to perform an air clean operation.

Figure 9:
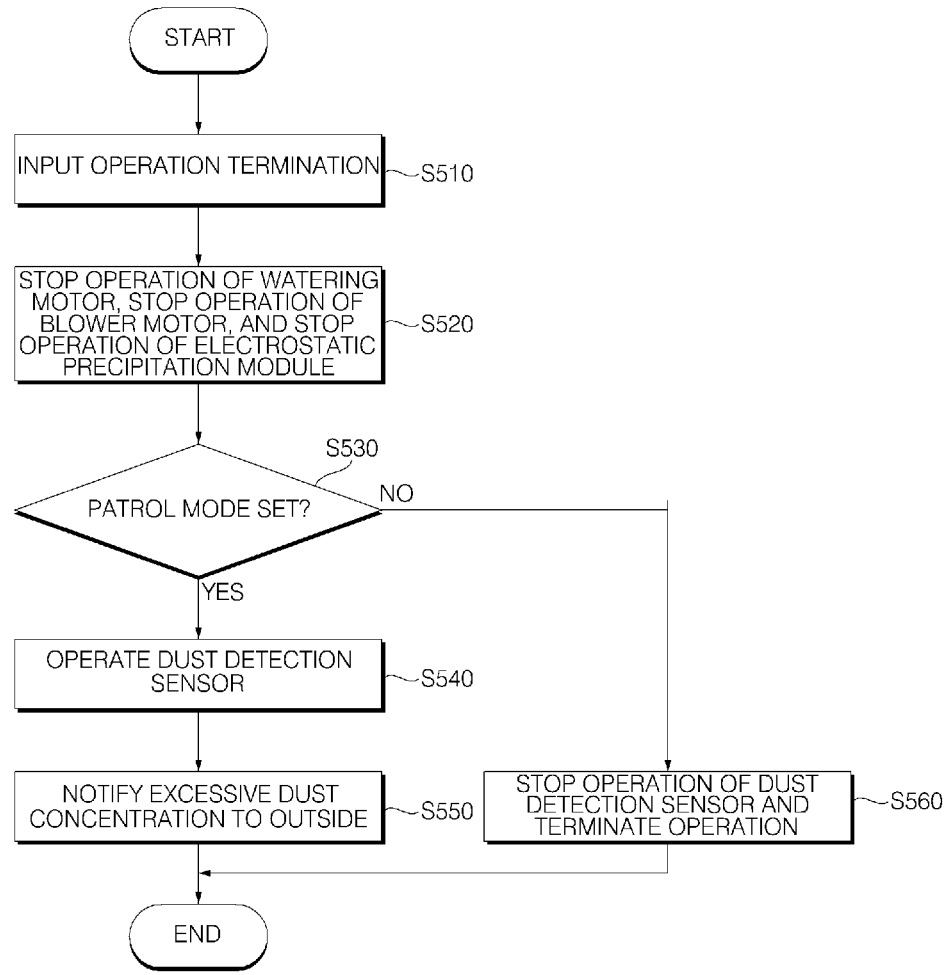
FIG. 9 is a flowchart illustrating a control method of an air conditioner according to another embodiment of the present invention.

FIG. 9 is a flowchart illustrating a control method of an air conditioner according to another embodiment of the present invention.

An instruction for terminating the entire operation may be inputted during an operation of the air conditioner in operation S510. When a user presses the power button 241 of the operation module 240 during an operation of the air conditioner, the operation module 240 may deliver an instruction for terminating the entire operation to the control unit 190.

Before the instruction for terminating the entire operation is inputted, the air conditioner may perform both a humidification operation and an air clean operation, or perform one of them. In this embodiment, description is made based on a case that an instruction for terminating the entire operation is inputted while both a humidification operation and an air clean operation are performed.

Once the entire operation termination instruction is inputted, the control unit 190 may stop an operation of the watering motor 42, stop an operation of the blower motor 22 and stop an operation of the electrostatic precipitation module 15 in operation S520. The control unit 190 may stop an operation of the watering motor 42 in order to allow the watering housing 44 to stop spraying water. The control unit 190 may stop an operation of the blower motor 22 to stop the rotation of the blower fan 24. The control unit 190 may stop an operation of the electrostatic precipitation module 15 in order to allow the electrostatic precipitation module 15 to stop charging foreign materials in air with electricity. Once the entire operation termination instruction is inputted, the control unit 190 may allow the display of the humidification display column 163*b* and the air clean display column 163*c* of the display unit 163 to disappear.

Before the entire operation termination, when only a humidification operation is performed, since the electrostatic precipitation module 15 is not in operation, the control unit 190 may not be required to stop an operation of the electrostatic precipitation module 15 separately.

Before the entire operation termination, when only an air clean operation is performed, since the watering motor 42 is not in operation, the control unit 190 may not be required to stop an operation of the watering motor 42 separately.

The control unit 190 may determine whether a patrol mode is set in operation S330. Before the entire operation termination instruction is inputted after the air conditioner operates, if a user presses the patrol button 245, the operation module 240 may deliver to the control unit 190 information that the patrol mode is inputted, and the control unit 190 may set the patrol mode and display on the patrol display column 163*e* of the display unit 163 information that the patrol mode is set. Once the entire operation termination instruction is inputted, the control unit 190 may determine whether the patrol mode is set.

According to an embodiment, when a user presses the patrol button 245 after the entire operation termination, the control unit 190 may determine whether the patrol mode is set in order to perform the following steps.

If the patrol mode is set, the control unit 190 may operate the dust detection sensor 135 in operation S540. Since the dust detection sensor 135 operates during the entire operation (for example, both the humidification operation and the air clean operation) or the air clean operation, when the patrol mode is set, the control unit 190 may operate the dust detection sensor 135 continuously. Before the entire operation termination, when only a humidification operation is performed, since the dust detection sensor 135 is not in operation, the control unit 190 may start an operation of the dust detection sensor 135.

When the control unit 190 operates the dust detection sensor 135, the dust detection sensor 135 may detect a dust concentration of external air flowing through the dust detection opening part 13*a*. The dust detection sensor 135 may detect a dust concentration by each dust particle size and in this embodiment, may distinguish and detect dust concentrations of PM 1.0, PM 2.5, and PM 10.0.

When the dust detection sensor 135 detects an excessive dust concentration, the control unit 190 may notify the outside that the dust concentration is excessive in operation S550. If a dust concentration in air is higher than a predetermined allowable concentration, the control unit 190 may notify it to the outside. The control unit 190 may determine whether a dust concentration in air is higher than a predetermined allowable concentration by each dust particle size.

If a dust concentration is excessive, the control unit 190 may emit light of a specific color through the lighting unit 165 to notify an excessive dust concentration to the outside. In this embodiment, the control unit 190 may allow the lighting unit 165 to emit red color light in order to allow a user to easily notice that a dust concentration is excessive.

When a dust concentration is excessive, the control unit 190 may display on the dust concentration display column 163*a* that the dust concentration is excessive. The control unit 190 may display "PM 1.0" or "ultra fine dust" when a dust concentration of PM 1.0 is excessive, display "PM 2.5" or "fine dust" when a dust concentration of PM 2.0 is excessive, and may display "PM 10.0" or "dust" when a dust concentration of PM 10.0 is excessive, on the dust concentration display column 163*a*.

If a dust concentration is excessive, the control unit 190 may transmit to a user's portable device that the dust concentration is excessive through the communication module 180. When receiving that the dust concentration is excessive, the portable device may display it on a screen to allow a user to easily notice that the dust concentration is excessive at a place where the air conditioner is installed.

The control unit 190 may notify to the outside that a dust concentration is excessive in order to induce a user to start an operation the air conditioner.

When the patrol mode is not set, the control unit 190 may completely terminate the entire operation in operation S560. When the dust detection sensor 135 is in operation, the control unit 190 may stop its operation. The control unit 190 may stop the display of the display unit 163 and the light emission of the lighting unit 165 and allow the air conditioner to enter a standby state.

An air conditioner and a control method thereof according to an exemplary embodiment of the present invention have at least one of the following effects.

First, by sterilizing and drying a humidification medium containing moisture when humidification is not performed, sanitation can be ensured.

Second, by generating ions and blowing air to a humidification medium, sterilization and drying can be performed effectively.

Third, by performing the sterilization and drying of a humidification medium only when a user provides a setting, an energy use that a user does not want can be suppressed.

Fourth, by sterilizing and drying a humidification medium only for a predetermined time, energy use can be minimized.

Fifth, even when only humidification is terminated and only air cleaning is performed, by sterilizing and drying a humidification medium, sanitation can be maintained.

The effects of the present invention are not limited to the above; other effects that are not described herein will be clearly understood by the persons skilled in the art from the following claims.

The above-disclosed subject matter is to be considered illustrative and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. An air conditioner comprising:
a water tank to store water;
a humidification medium disposed above the water tank;
a watering housing to draw and spray the water stored in the water tank to supply the water to the humidification medium;
a watering motor to rotate the watering housing;
a visual body coupled to an upper part of the water tank to reflect and scatter the water sprayed from the watering housing;
a top cover assembly disposed at an upper end of the visual body, the top cover assembly having an outlet through which air is discharged;
a blower fan to blow air to the humidification medium;
a blower motor to rotate the blower fan;
an operation module to receive an instruction from a user and to set a sterilizing dry mode for sterilizing and drying the humidification medium;
a sterilization module to sterilize the humidification medium; and
a control unit to control the watering motor, the blower motor, and the sterilization module according to an instruction inputted to the operation module,
wherein the humidification medium comprises a material that is capable of containing moisture,
wherein the control unit stops an operation of the watering motor according to an instruction inputted to the operation module, operates the blower motor and the sterilization module when the sterilizing dry mode is set, and stops the operation of the sterilization module after a predetermined sterilizing dry time elapses,
wherein the watering housing comprises a nozzle for spraying water to an inner side surface of the visual body to supply moisture to the humidification medium,
wherein the nozzle is disposed higher than the humidification medium, and
wherein when blower motor is operated, air blown by the blower fan flows into a space formed between the visual body and the water tank, passes the humidification medium, and is discharged through the outlet.

2. The air conditioner of claim 1, wherein:
the sterilization module comprises an ion generation module to generate ions;
the control unit operates the ion generation module when operating the sterilization module; and
the control unit stops an operation of the ion generation module when stopping an operation of the sterilization module.

3. The air conditioner of claim 1, wherein:
the sterilization module comprises an ultraviolet module to emit ultraviolet rays;
the control unit operates the ultraviolet module when operating the sterilization module; and
the control unit stops an operation of the ultraviolet module when stopping an operation of the sterilization module.

4. The air conditioner of claim 1, wherein when an operation time of the watering motor is longer than a predetermined humidification operation time before the control unit stops an operation of the watering motor, the control unit operates the blower motor and operates the sterilization module.

5. The air conditioner of claim 1, wherein when an operation termination instruction is inputted to the operation module, the control unit stops an operation of the watering motor; and the control unit stops an operation of the blower motor when stopping an operation of the sterilization module.

6. The air conditioner of claim 5, further comprising an electrostatic precipitation module to charge foreign materials in air with electricity to clean the air, wherein the control unit stops an operation of the electrostatic precipitation module when stopping an operation of the watering motor.

7. The air conditioner of claim 1, wherein when a humidification termination instruction is inputted to the operation module, the control unit stops an operation of the watering motor.

8. The air conditioner of claim 1, further comprising a display unit to display a state of the air conditioner, wherein when the sterilizing dry mode is set through the operation module, the control unit displays on the display unit that the sterilizing dry mode is set.

9. A control method of an air conditioner of claim 1, the method comprising:
  stopping an operation of a watering motor to stop supplying water to a humidification medium is formed of a material that is capable of containing moisture;
  blowing air to the humidification medium and sterilizing the humidification medium, when a sterilizing dry mode for sterilizing and drying the humidification medium is set; and
  stopping the sterilizing of the humidification medium after a predetermined sterilizing dry time elapses.

10. The method of claim 9, wherein the sterilizing of the humidification medium comprises generating ions to sterilize the humidification medium.

11. The method of claim 9, wherein the sterilizing of the humidification medium comprises emitting ultraviolet rays.

12. The method of claim 9, further comprising, when an operation time of the watering motor is longer than a predetermined humidification operation time before an operation of the watering motor stops, blowing air and sterilizing the humidification medium.

13. The method of claim 9, further comprising, when an operation termination instruction is inputted, stopping an operation of the watering motor, and when the sterilization stops, stopping an operation of the blower motor.

14. The method of claim 13, further comprising, when an operation of the watering motor stops, stopping an operation of an electrostatic precipitation module to stopping charging foreign materials in air.

15. The method of claim 9, further comprising, when a humidification termination instruction is inputted, stopping an operation of the watering motor.

* * * * *